United States Patent

Plant Pat. 3,835

Patented Mar. 2, 1976

3,835

ORCHID PLANT (REALITE)

Maurice Lecoufle and Michel Vacherot, Boissy-St.-Leger, France, assignors to Les Petits-Fils et Fils de Vacherot & Lecoufle, Boissy-St.-Leger, France Filed Nov. 20, 1974, Ser. No. 525,404

Claims priority, application France, Nov. 29, 1973, 42,578

Int. Cl. A01h *5/00*

U.S. Cl. Plt.—68 1 Claim

ABSTRACT OF THE DISCLOSURE

A new variety of orchid plant of the species Cymbidium characterized by its vigorous and rapidly multiplying growth habit which produces floriferous plants of medium size having many erect stems of excellent appearance thus permitting a good planting density and abundant production for a given growing area. The flowers are spaced regularly and their relatively long peduncles permit them to be well separated, and the plant flowers regularly from mid-November to the end of December with blossoms having petals and sepals with a background color of spinel red mixed with a suffusion of light yellow and a labellum of stronger yellow bordered by a train of Oxblood spots.

BACKGROUND OF THE INVENTION

Our new variety of orchid plant was selected from a group of seedlings resulting from a crossing of Cymbidium Kurun (unpatented) and Redwood (unpatented) made by us at Boissy-Saint-Leger, France, with the objective of improving the already remarkable qualities of Cymbidium Kurun and developing an early hybrid which would flower regularly from mid-November to the end of December, with full production about mid-December, in order to supply the heavy end-of-year demand. This plant was selected by us for propagation because of its exception qualities which largely fulfilled our desires and asexual reproduction of the plant by meristematic tissue culture has been carried on by us at Boissy-Saint-Leger, France. Successive generations of mericlones of this new orchid plant have demonstrated that all of its distinctive and advantageous characteristics hold true from generation to generation and appear to be firmly fixed.

As the generic identification of our new orchid plant, we have adopted the name Realite and for its commercial exploitation, this cultivar is to be known as Velecab.

DESCRIPTION OF THE DRAWINGS

This new variety of orchid plant is illustrated by the accompanying drawings, in which.

DESCRIPTION OF THE NEW VARIETY OF ORCHID PLANT

Figure 1:
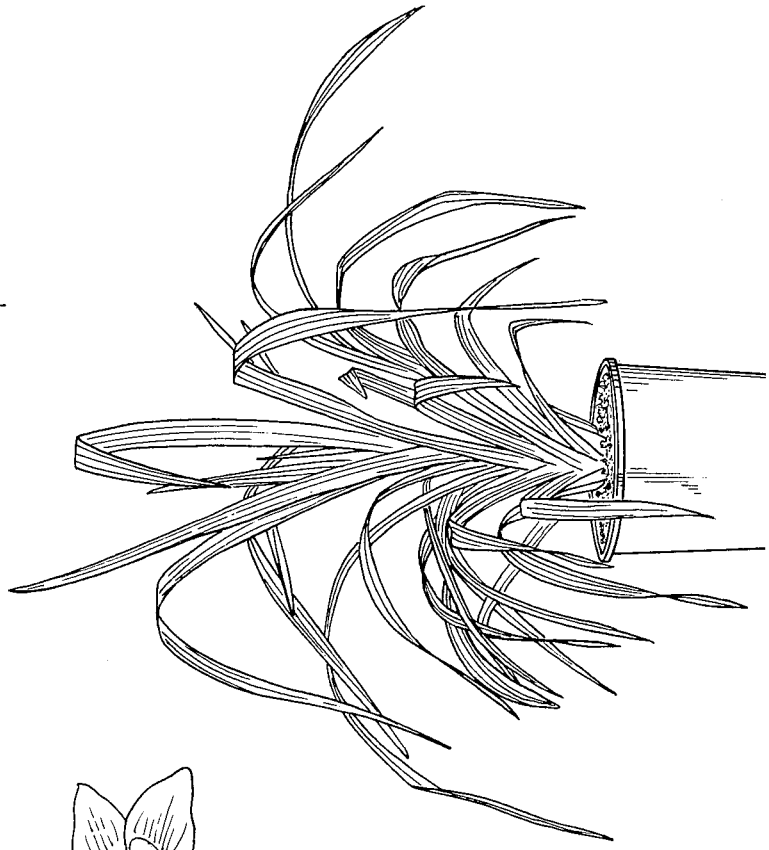
FIG. 1 is a sketch which shows a typical adult plant of the cultivar.
Figure 2:
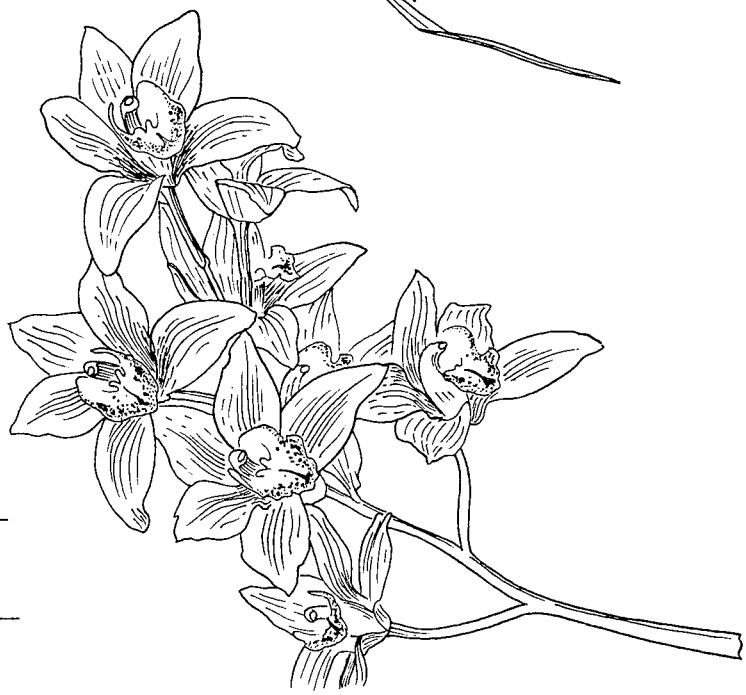
FIG. 2 is a sketch showing a stem of the plant with open flowers.
Figure 3:
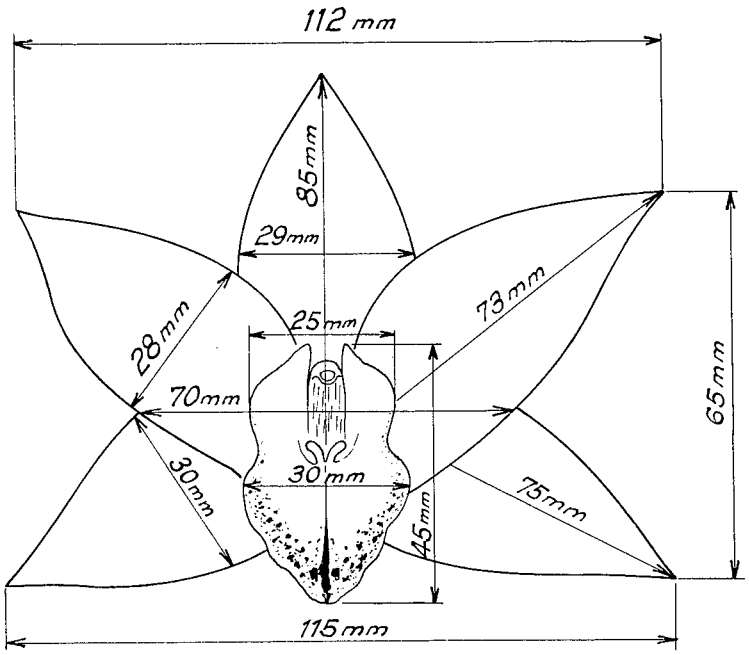
FIG. 3 is a diagrammatic view showing details of a flower of this cultivar.
Figure 4:
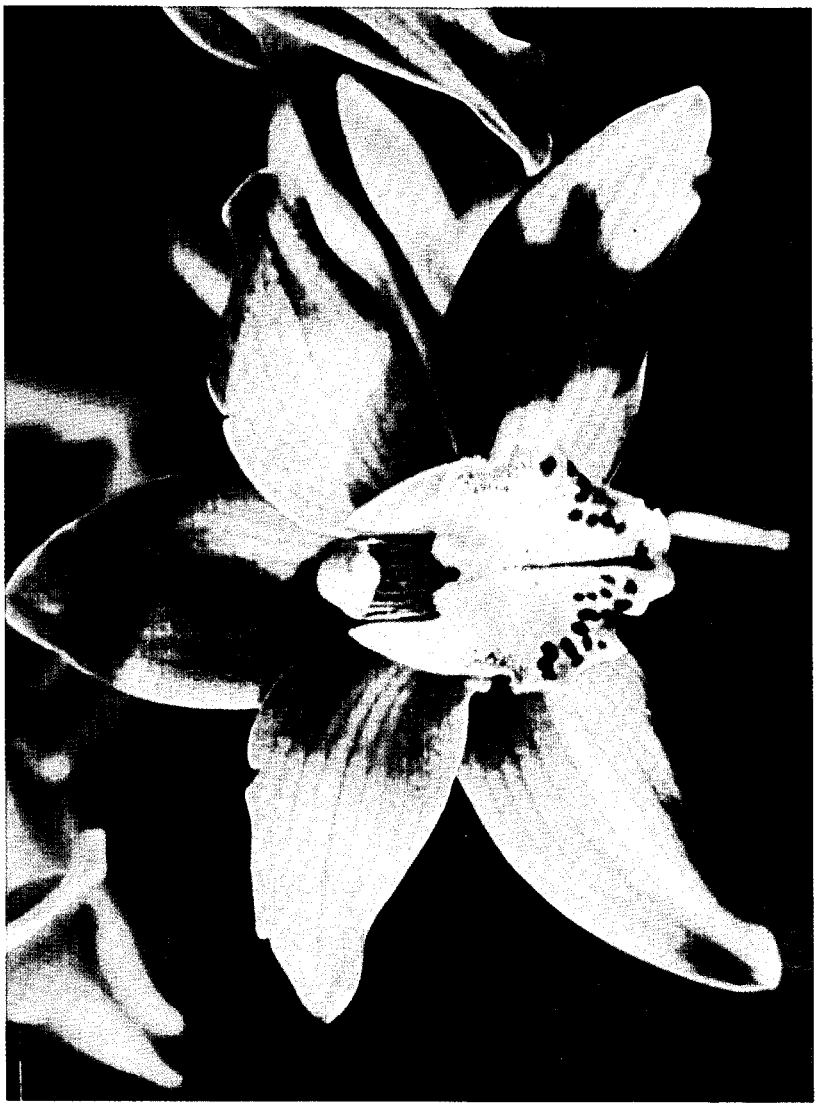
FIG. 4 is a photographic drawing in full color showing the flower of this cultivar, the color reproduction being as accurate as is reasonably possible to obtain by commercial photographic procedures.

The following is a detailed description of our new variety of orchid plant with color designations according to the Horticultural Colour Chart (HCC) and the R.H.S. Colour Chart (RHS) published by The Royal Horticultural Society at London, England.

The plant

When young, the plant is not particularly distinguishable from several other Cymbidium plants. When the plant is adult, however, it has special characteristics which distinguishes the plant from all others.

Origin: Seedling.

Parentage:

*Seed parent.*—Cymbidium Kurun (unpatented).

*Pollen parent.*—Cymbidium Redwood (unpatented).

Classification:

*Botanic.*—Cymbidium hybrid.

*Commercial.*—Cymbidium mericlone.

Form: Herbaceous.

Height:

*Flower stem.*—80 to 90 cm.

*Leaves.*—To about 100 cm.

Bulb: Number—A plant is adult when it has 3 well formed bulbs with leaves. Bulbs increase in number each year thereafter.

*Size.*—The primary bulb, the front bulb of the adult plant, is about 6 cm. in width.

*Stems.*—The primary bulb of the adult plant carries one or two flowering stems. As the plant develops further, the bulb may have only one stem or sometimes develop more than two.

Foilage: Number of leaves—Each bulb of the adult plant has five pairs of alternately opposed leaves.

*Size of leaves.*—Length—From 35 to 100 cm. Sometimes longer. Width—3 cm. at largest part.

*Petioles.*—The base of each leaf, where attached to the bulb, is about 15 cm. long and is of a slightly different color than the leaves due to anthrocyanins.

A callus in the form of a dark line or bar forms the junction of the petioles and the leaf.

*Venation.*—From base to tip.

*Color.*—The leaf is of a dark green color and has a well accentuated central rib. The petiole is of a slightly lighter green color and has inwardly curved margins.

*Stems.*—The flowering stem is usually from 80 to 90 cm. in length. The first flower is at about 45 to 50 cm. from the base of the stem which is surrounded with amplexicaul bracts from the base to the first flower.

The flower

Blooming habit: Recurrent. The plant flowers regularly from mid-November until the end of December with full production occurring about the 10th to 15th of December.

Borne: In a racemose manner on a stem of about 80 to 90 cm. long, each flower being carried by a peduncle forming an acute angle with the stem. The first flower appears at about 45 to 50 cm. from the base of the stem and the distance between the flowers, which can be alternate, can range between 0 and 75 cm. The adult plant produces about 15 flowers on each stem and at each flower peduncle there is an amplexicaul bract embryo which for the first flower is quite long and for the last flower extremely short.

Average size: Large. 115 mm. between the tips of the two lateral sepals; 112 mm. between tips of the two petals; and 65 mm. between the tips of adjacent petals and sepals.

*Sepals.*—Length—75 mm. Width: Lateral sepals—30 mm. Dorsal sepal—29 mm.

*Petals.*—Length—73 mm. Width—29 mm.

*Labellum.*—45 mm. long and 30 mm. wide across the center.

*Gynostemium.*—Length—40 to 45 mm.

*Shape of sepals and petals.*—Generally elliptic with acute and acuminate outer ends terminating in sharp points.

Color:

*Petals and sepals.*—A mixture of Spinel Red 0023/1 (HCC), 54B (RHS), with a suffusion of very light yellow for background color, the whole being veined from base to tip with thin lines of Oxblood Red 00823/3 (HCC), 183C (RHS), the reverse side of the sepals being particularly dark and, in general, the dark red color of the veins providing an overall appearance for the top side of the corolla somewhat darker than the background coloring.

*Labellum.*—Light Yellow, shaded with the same color as the sepals near the margins and having a central stripe about 2 cm. long, extending inwardly from near the outer end, colored Oxblood Red 00823/3 (HCC), 183C (RHS), and being freckled around the margins with spots of the same color.

*Gynostemium.*—The uppermost central part, on the upper side, is entirely of the same color as the labellum, while the lateral parts are almost colorless where they are covered by the lateral wings of the labellum. The under side of the gynostemium is marked with spots of the same color as the upper side of the labellum.

Peduncle: Length—In general, about 55 to 65 mm. The last flower has a long peduncle extending upwardly about 10 to 12 cm. to terminate the stem.

A cytological study of this plant has shown it to be diploid, a characteristic which is distinctive of this new orchid variety.

Outstanding and distinctive characteristics are to be found in its vigorous growth and rapid bulb producing habit and in its medium size which permits good planting density. Other distinctive features reside in its very floriferous habit which produces many erect stems having regularly spaced and well separated flowers on relatively long peduncles. The characteristics of the flower itself are outstanding in that it is an early variety of very good size and of excellent texture, lasting quality and coloration.

It will be understood that the measurements and colors of this new orchid plant can vary to a considerable extent depending upon the conditions of growth and the quantity of light given to the flower.

We claim:

1. A new and distinct variety of orchid plant of the Cymbidium species, substantially as herein shown and described, characterized by its vigorous growth and rapid bulb producing habits, its abundant production of large regularly spaced flowers having long peduncles, its attractive coloration, and mid-November to end of December flowering with full production about mid-December.

No references cited.

ROBERT E. BAGWILL, Primary Examiner.